United States Patent [19]

Stone

[11] Patent Number: 5,258,043
[45] Date of Patent: Nov. 2, 1993

[54] METHOD FOR MAKING A PROSTHETIC INTERVERTEBRAL DISC

[75] Inventor: Kevin R. Stone, San Francisco, Calif.

[73] Assignee: ReGen Corporation, San Francisco, Calif.

[21] Appl. No.: 813,984

[22] Filed: Dec. 26, 1991

Related U.S. Application Data

[60] Division of Ser. No. 520,027, May 7, 1990, Pat. No. 5,108,438, which is a continuation-in-part of Ser. No. 317,951, Mar. 2, 1989, Pat. No. 5,007,934, which is a continuation-in-part of Ser. No. 75,352, Jul. 20, 1987, Pat. No. 4,880,429.

[51] Int. Cl.$^5$ .............................. A61F 2/02; A61F 2/44
[52] U.S. Cl. .................................. 623/66; 623/17; 623/16
[58] Field of Search ............... 623/16, 11, 18, 17, 623/13, 15, 66, 1

[56] References Cited

U.S. PATENT DOCUMENTS

| | | | |
|---|---|---|---|
| 3,551,560 | 12/1970 | Thiele | 424/95 |
| 3,855,638 | 12/1974 | Pilliar | 3/1 |
| 3,875,595 | 4/1975 | Froning | 3/1 |
| 4,060,081 | 11/1977 | Yannas et al. | 128/156 |
| 4,085,466 | 4/1978 | Goodfellow et al. | 3/1.91 |
| 4,280,954 | 7/1981 | Yannas et al. | 260/123.7 |
| 4,344,193 | 8/1982 | Kenny | 3/1.911 |
| 4,349,921 | 9/1982 | Kuntz | 3/1 |
| 4,350,629 | 9/1982 | Yannas et al. | 260/123.7 |
| 4,378,224 | 3/1983 | Nimni et al. | 8/94 |
| 4,400,833 | 8/1983 | Kurland | 3/1 |
| 4,418,691 | 12/1983 | Yannas et al. | 128/156 |
| 4,448,718 | 5/1984 | Yannas et al. | 260/123.7 |
| 4,458,678 | 7/1984 | Yannas et al. | 128/155 |
| 4,505,266 | 3/1985 | Yannas et al. | 128/1 R |
| 4,544,516 | 10/1985 | Hughes et al. | 264/108 |
| 4,578,079 | 3/1986 | Ruoslahti et al. | 623/11 |
| 4,589,881 | 5/1986 | Pierschbacher et al. | 623/11 |
| 4,614,794 | 9/1986 | Easton et al. | 530/356 |
| 4,627,853 | 12/1986 | Campbell et al. | 623/16 |
| 4,661,111 | 4/1987 | Ruoslahti et al. | 623/11 |
| 4,772,287 | 9/1988 | Ray et al. | 623/17 |
| 4,787,900 | 11/1988 | Yannas | 623/1 |
| 4,801,299 | 1/1989 | Brendel et al. | 623/1 |
| 4,837,285 | 6/1989 | Berg et al. | 530/356 |

FOREIGN PATENT DOCUMENTS 0277678 8/1988 European Pat. Off. .
8910728 11/1989 PCT Int'l Appl. .

OTHER PUBLICATIONS

Gross et al. "Bone-induction potential of mineralized collagen gel xenografts", vol. 49 (No. 1), Oral Surg., Jan. 1980, pp. 21-26.
Cleveland (1955) Marquette Med. Rev. 20:62.
Hamby et al. (1959) J. Neurosurg. 16:311-313.
Fernström (1973) Acta Chir. Scand. 4:154-159.
Urbaniak et al. (1973) J. Biomec. Meter. Res. Symposium 4:165-186.
Schneider et al. (1974) Z. Orthop. 112:1078-1086.
Alitalo (1979) Acta Veterinaria Scandinavica Suppl. 71:1-58.
Yannas (1979) Am. Chem. Soc. 16:1-9.
Albrektsson et al. (1981) Acta Orthop. Scan. 52:155-170.
Edeland (1985) J. Biomed. Eng. 7:57-62.
Leenslag et al. (1986) Biolog. and Biomech. Perf. Biomaterials, (Christel et al., eds.) Elsevier Sci. Publishers B.V., Amsterdam.
Petite et al. (1990) J. Biomed. Materials Res. 24:179-187.

*Primary Examiner*—David Isabella
*Attorney, Agent, or Firm*—Lahive & Cockfield

[57] ABSTRACT

A prosthetic intervertebral disc is disclosed which can be implanted in the human skeleton, and which can act as a scaffold for regrowth of intervertebral disc material. The disc includes a dry, porous, volume matrix of biocompatible and bioresorbable fibers which may be interspersed with glyscosaminoglycan molecules. The matrix is adapted to have in vivo an outer surface contour substantially the same as that of a natural intervertebral disc, whereby the matrix establishes an at least partially bioresorbable scaffold adapted for ingrowth of intervertebral fibrochondrocytes. Cross-links may be provided by a portion of the GAG molecules.

16 Claims, 3 Drawing Sheets

METHOD FOR MAKING A PROSTHETIC INTERVERTEBRAL DISC

This is a divisional application of application Ser. No. 520,027, filed May 7, 1990 (now U.S. Pat. No. 5,108,438), which is a continuation-in-part of application Ser. No. 317,951, filed Mar. 2, 1989 (now U.S. Pat. No. 5,007,934), which is a continuation-in-part of application Ser. No. 075,352, filed Jul. 20, 1987 (now U.S. Pat. No. 4,880,429).

BACKGROUND OF THE DISCLOSURE

The present invention is in the field of implantable medical devices, and more particularly, is directed to devices useful as a prosthetic intervertebral disc.

The intervertebral disc acts in the spine as a crucial stabilizer, and as a mechanism for force distribution between the vertebral bodies. Without the disc, collapse of the intervertebral space occurs in conjunction with abnormal joint mechanics and premature development of arthritic changes.

Prior art methods of treating injured or diseased discs have included chemical disintegration procedures and surgical excision, often followed by bony fusion to prevent spinal collapse or instability. With excision, no significant regeneration of vertebral tissue occurs. Replacement of an injured disc in an otherwise healthy spine may prevent arthritic changes and may stabilize the spinal segments. In diseased spines, replacement of the disc may reduce the progression of the disease process, and may provide pain relief.

In alternative prior art replacement approaches, discs have been replaced with prostheses composed of artificial materials. The use of purely artificial materials in the spine minimizes the possibility of an immunological response. In addition, such materials permit construction of a structure which can withstand the high and repeated loads seen by the spinal vertebral joints, and can alter the joint mechanics in beneficial ways that biological materials would not tolerate. For example, titanium, (Albrektsson et al. (1981) Acta Ortop. Scan. 52:155–170), acrylic (Cleveland (1955) Marquette Med. Rev. 20:62; Hamby et al.(1959) J. Neurosurg. 16:311), polytetrafluorothylene-carbon fiber (Alitalo (1979) Acta Veterinaria Scandinavica Suppl. 71:1–58), and steel discs (Fenrstrom (1973) Acta Chir. Scand. 4:165–186; have been used to replace the resected disc. Each of these efforts have met with failure due to continued collapse of the disc space or erosion of the metal prosthesis into the surrounding bone.

A prosthetic intervertebral disc has also been constructed from resilient materials such as silicone rubber (e.g., Edeland (1985) J. Biomed Eng. 7:57–62; Schneider et al. (1974) Z. Orthop. 112:1078–1086; Urbaniak et al. (1973) J. Biomed. Mater. Res. Symposium 4:165–186). A disc has also been made from resilient plastic materials to form a bladder as disclosed in U.S. Pat. Nos. 3,875,595 and 4,772,287; however, failure to restore full stability and normal joint biomechanics has prevented success. Porous elastomeric materials as described in U.S. Pat. No. 4,349,921 have failed to recapitulate the normal vertebral body mechanics.

Generally, the replacement of intervertebral tissue with structures consisting of artificial materials has been unsuccessful principally because the opposing vertebral end plates of human and animal joints are fragile. The end plates in the spine will not withstand abrasive interfaces nor variances from normal compliance, which evidently result from the implantation of prior art artificial discs. Additionally, joint forces are multiples of body weight which, in the case of the spine, are typically over a million cycles per year. Thus far, prior art artificial discs have not been soft or durable enough, nor have they been able to be positioned securely enough to withstand such routine forces.

Prostheses, in general, have been devised out of at least some of the constituents of the structures which they are replacing, or out of materials not considered to be immunogenic to the body. For example, Yannas et al. fashioned blood vessel grafts (U.S. Pat. No. 4,350,629), synthetic epidermis (U.S. Pat. No. 4,448,718), and sciatic nerve guides (WO 89/10728; Yannas (1979) Am. Chem. Soc. 16:209) out of collagen and glycosaminoglycans, biochemical components of many body organs. By adjusting the pore size and axes of the pores and fibers comprising these structures, regrowth of natural tissue could be stimulated. Further regrowth has been advanced by seeding of the nerve guide with Schwann cells prior to implantation (see U.S. Pat. No. 4,458,678). However, even with the foregoing technologies which have been applied to the reconstruction of anatomical structures other than intervertebral discs, a structure suitable as a prosthetic disc and constructed from natural materials has not yet been successfully developed.

Accordingly, it is an object of this invention to provide an intervertebral disc replacement or prosthesis.

Another object is to provide an improved disc replacement or prosthesis that does not interfere with normal vertebral segment motion as such interference could lead to a reduced range of motion or to focal concentration of force at other sites within the spinal column or instability of the opposing vertebral bodies, therefore enhancing the chances of progressive arthritic destruction.

Yet another object is to provide an improved disc replacement or prosthesis that is biomechanically able to withstand normal spinal column forces and is able to function at those loads to protect the opposing end plates and stabilize the joints.

Still another object is to provide an improved disc replacement or prosthesis which promotes regrowth of intervertebral disc material and which acts as a scaffold for fibrocartilage infiltration.

A further object is to provide an improved disc replacement or prosthesis which does not evoke an immunologic reaction or aggravate other joint structures.

Still a further object is to provide an improved intervertebral disc replacement or prosthesis which can be easily implanted by standard operative techniques.

SUMMARY OF THE INVENTION

The present invention provides a biocompatable and bioresorbable structure for implantation into the spine which assumes the form and role of an intervertebral disc. This matrix may promote regrowth of intervertebral fibrochondrocytes and provides a scaffold for the regenerating intervertebral disc tissue.

The prosthetic disc is composed of a dry, porous, volume matrix of biocompatible and bioresorbable fibers. The matrix is adapted to have in vivo an outer surface contour substantially the same as that of a natural intervertebral disc. A portion of the fibers may be cross-linked.

The fibers include a natural fiber or an analog of a natural fiber such as a biosynthetic analog, or a synthetic fiber, or mixtures thereof. A biosynthetic fiber is one which may be produced by recombinant DNA technology including the transfection of an appropriate host cell capable of protein expression with a gene encoding, for example, a recombinant protein such as collagen. A synthetic fiber is one which may be produced by chemical methods such as automated peptide synthesis. In one preferred embodiment of the invention, the fibers of the matrix are polymers of, for example, natural molecules such as those obtained from animal or human tissue. Natural fibers useful for the same purpose preferably include collagen, elastin, reticulin, analogs thereof, and mixtures thereof.

In some forms of the invention, the fibers may be randomly orientated throughout the matrix, or may be ordered at specified regions. Alternatively, the fibers may assume substantially circumferentially extending or substantially radially extending orientations throughout the prosthetic disc.

The matrix may also include glycosaminoglycan molecules (GAGs) interspersed with the fibers. GAGs are mucopolysaccharide molecules which provide lubrication and may be included in cross-links for the prosthetic disc. In one preferred aspect of the invention, GAGs such as chondroitin 4-sulfate, chondroitin 6-sulfate, keratin sulfate, dermatan sulfate, heparan-sulfate, heparin, hyaluronic acid, and mixtures thereof form a component of the disc. The GAGs may be uniformly dispersed throughout the prosthetic disc as individual molecules, or may be present in varying amounts in different regions of the structure.

In various forms of the invention, GAGs may directly participate in covalent cross-linking with the fibers, or may interact with the fibers mechanically in the form of entanglement or through interlocking mechanisms, thereby forming various stable fiber-GAG complexes.

The matrix may include about 75-100% natural and/or synthetic fibers and about 0-25% GAGs by dry weight, the proportions of which may be constant throughout the structure or may be variable.

In a preferred embodiment of the invention, the matrix has a density of about 0.07 to 0.50 g matrix/cm$^3$, where "g matrix/cm$^3$" is a unit connoting the number of grams in a cubic centimeter of the matrix. In addition, the matrix may have an interfibrillary and intrafibrillary space of about 2 to 25 cm$^3$/g matrix.

In another form of the invention, the prosthetic disc may further include a mesh composed of a bioresorbable, biocompatible material which is attached to lateral portions of the outer surface of the matrix. The mesh aids in the successful implantation of the prosthetic intervertebral disc into the intervertebral spaces by providing a temporary anchoring mechanism.

The present invention also includes a method of regenerating intervertebral disc tissue in vivo. This method includes fabricating a prosthetic intervertebral disc of the type described above, and implanting it into the spine by surgical procedures. The presence of the prosthetic disc stimulates disc tissue growth.

Further, the invention includes a method for fabricating a prosthetic intervertebral disc of the type described above. Generally, the method includes placing a plurality of fibers or fibers and GAGs into a mold having a shape useful for spine function, subjecting the fibers (and GAGs) in the mold to two cycles of freezing and thawing, contacting the fibers or the fibers and GAGs with a chemical cross-linking reagent such that the fibers then assume the shape of the mold, and lyophilizing the resulting structure to obtain a dry, porous, volume matrix.

The fibers may be laid down in a circumferential orientation by rotating the mold as they are placed therein. Alternatively, the fibers in the mold may be compressed with a rotating piston. Radial orientation of the fibers is produced by manually painting the fibers in a linear, radially directed fashion.

Specific densities and pore sizes may be obtained in various regions of the matrix by compressing the fibers or fibers and GAGs in the mold prior to the second freeze-thaw cycle, and subsequent to the chemical cross-linking step. This may be accomplished by applying pressure to a specific region of the matrix with a piston of a predetermined shape.

In a preferred aspect of the invention, the cross-linking step is performed using chemical agents which form intramolecular and intermolecular cross-links. Useful chemical agents include, for example, glutaraldehyde, formaldehyde, biocompatible bifunctional aldehydes, carbodiimides, hexamethylene diisocyanate, bis-ionidates, glyoxal, polyglycerol polyglycidyl ether, glyoxal, and mixtures thereof. Particularly useful cross-linking agents are 1-ethyl, 3-(3-dimethylaminopropyl), polyglycerol polyglycidyl ether, acyl azide, and glutaraldehyde.

In other aspects of the invention, an additional cross-linking step is performed by lyophilizing the chemically cross-linked disc and then subjecting it to dehydrothermal cross-linking procedures.

The invention will next be described in connection with certain illustrated embodiments. However, it should be clear that various modifications, additions, and deletions can be made without departing from the spirit or scope of the invention.

BRIEF DESCRIPTION OF THE DRAWINGS

The foregoing and other objects of this invention, the various features thereof, as well as the invention, itself, may be more fully understood from the following description, when read together with the accompanying drawings in which.

DESCRIPTION OF THE INVENTION

It has been discovered that a prosthetic intervertebral disc fabricated from biocompatible and bioresorbable fibers can be surgically implanted into the intervertebral space so as to provide normal joint motion and strength. This prosthetic intervertebral disc also acts as a scaffold for regenerating disc tissue whose ingrowth is encouraged by the physical characteristics of the implanted device. Following implantation, tissue ingrowth, regeneration, and finally resorption of the scaffold, natural intervertebatal tissue remains.

Figure 1:
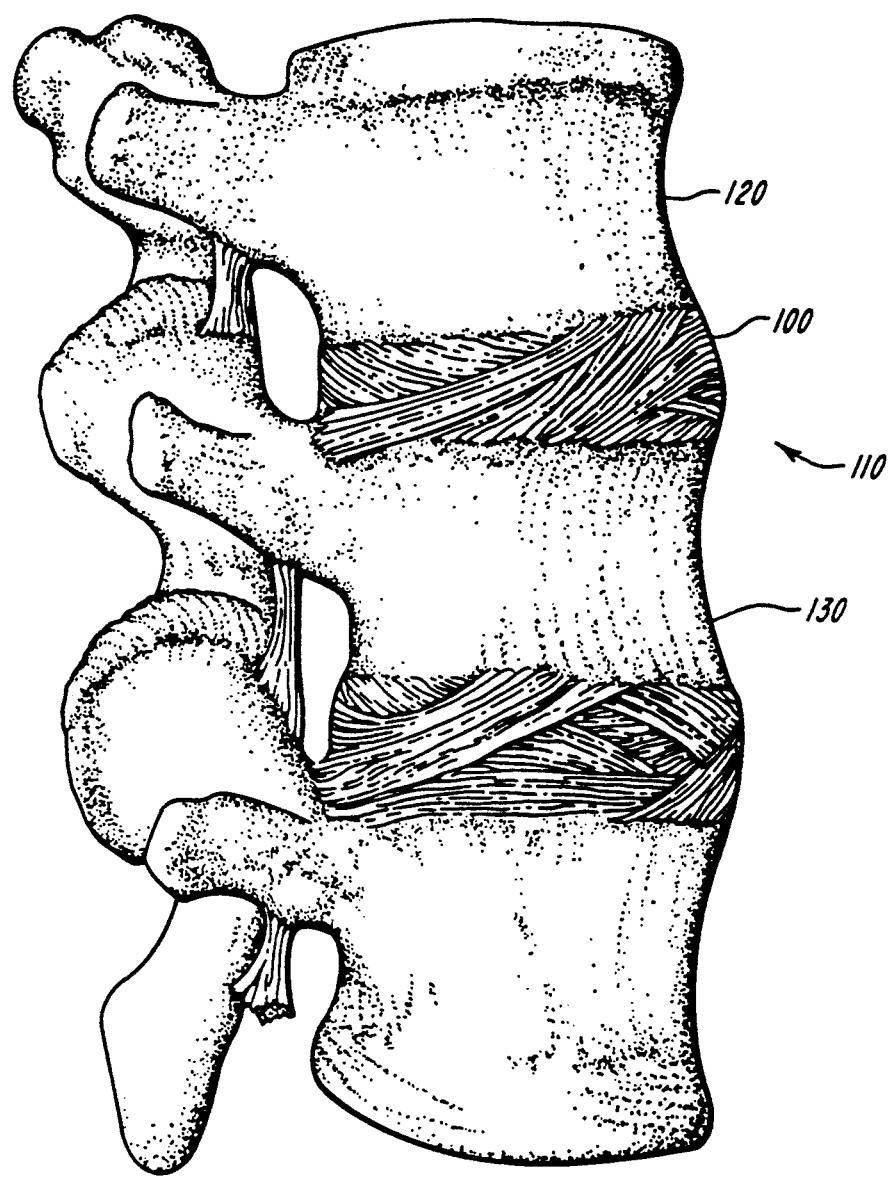
FIG. 1 is a simplified diagrammatic representation of the normal positioning of an intervertebral disc in native position in the human spine.
Figure 2:
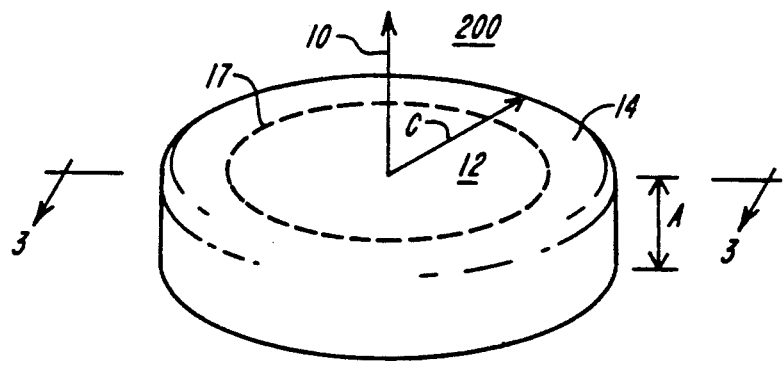
FIG. 2 shows a perspective view of an exemplary prosthetic intervertebral disc in accordance with the present invention.

FIG. 1 shows the normal positioning of an intervertebral disc 100 in the human intervertebral space 110 between the vertebral bodies 120 and 130. An exemplary prosthetic intervertebral disc 200 is shown in FIG. 2. The disc 200 is a generally porous, dry volume matrix which extends circumferentially in about a central axis 10. As used herein, the term "volume matrix" refers to a porous array characterized by relatively comparable (but not necessarily equal) outer dimensions in three orthogonal directions (as contrasted with a sheet matrix which would have relatively comparable dimensions in two orthogonal directions but relatively small dimensions in a third orthogonal direction).

Figure 3:
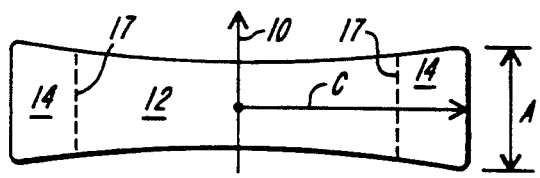
FIG. 3 shows a sectional view along line 3—3 of the prosthetic intervertebral disc of FIG. 2.

In the preferred form, prior to implantation, the prosthetic intervertebral disc 200 has the shape of a cylindrical pad, extending circumferentially about the axis 10, and comprising a relatively high compliance central region 12 disposed about a relatively low compliance peripheral region 14. In FIG. 2, the separation of regions 14 and 16 is indicated generally by broken line 17, although the transition is normally gradual. In the preferred form, the top and bottom (as shown) surfaces of disc 200 are concave so that disc 200 has maximum height A at its peripheral edge of approximately 8 mm and a maximum radial dimension C of approximately 35 mm. FIG. 3 shows a sectional view along line 3—3 of the prosthetic disc 200 shown in FIG. 2.

Figure 4:
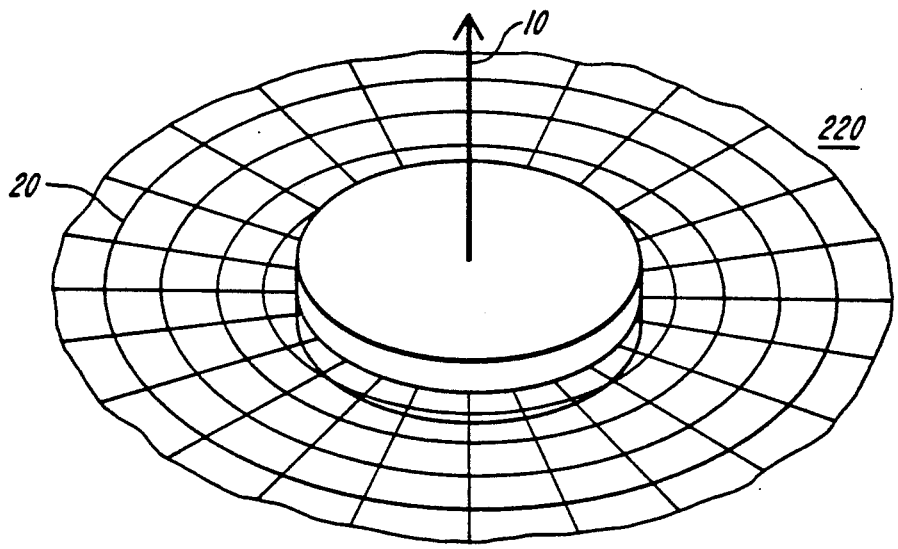
FIG. 4 shows a perspective view of another exemplary prosthetic intervertebral disc.

FIG. 4 shows an additional embodiment 220 of the present invention which is similar in composition to the prosthetic disc 200 depicted in FIG. 2. The prosthetic intervertebral disc 220 is similar to disc 200, but includes convex top and bottom surfaces and further includes a mesh member 20 extending from its lateral surface. The mesh member 20 is composed of a biocompatible, bioresorbable material. Following implantation, the mesh member 20 may be sutured to adjacent tissue to anchor the disc 220 in place. The mesh member 20 may function in this capacity until sufficient tissue ingrowth occurs to provide that function. Since the anchor function of mesh member 20 is only temporary, the mesh member 20 may be a #1 mesh screen composed of absorbable suture materials such as polyglyconate, Dexon, or polydioxane (PDS) woven into a mesh. Alternatively, nonabsorbable suture materials such as expanded polytetrafluoroethylene (PTFE) may be used.

Figure 5A:
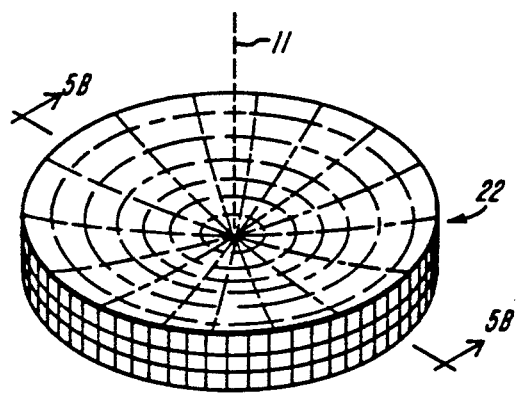
FIG. 5A shows a perspective view of another exemplary prosthetic intervertebral disc including a mesh member.
Figure 5B:
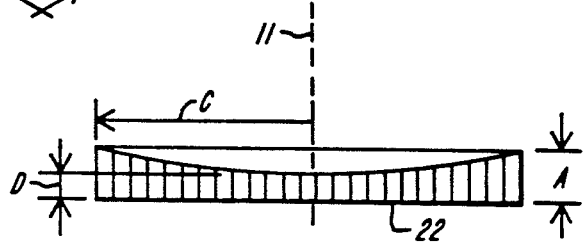
FIG. 5B shows a sectional view along line 5B—5B of the prosthetic disc of FIG. 5A.

FIGS. 5A and 5B show yet another embodiment 230 which is similar to that of FIG. 1 but having concave top and flat bottom surfaces. Other combinations might also be used.

In alternative forms of the invention, still other shapes than full cylinders may be used. For example, it is not required that the full 360° (about axis 10) pad be used if partial disc replacement is undertaken. For angular segment type discs, the cylindrical form may subtend any angle between zero and 360 degrees about axis 10. It is however important that the matrix have characteristics so that when implanted, at least the top and bottom surfaces substantially assume the shape or contour of a natural intervertebral disc.

The various embodiments of the invention may have certain densities of collagen fibers and dispersions of GAG molecules and cross-links that permit accommodation of differing stress levels, rates of ingrowth, and resiliency. Differing densities may be obtained in vivo where a device having uniform density is implanted, and body loading causes non-uniform compression of the device. Alternatively, the prosthetic disc may be initially configured with non-uniform construction of a type so that the in vivo configuration provides the desired spatial densities and dispersions necessary for the desired function.

The prosthetic intervertebral disc may be fabricated of any biocompatible, bioresorbable fibers such as a natural material, an analog thereof or a synthetic material. The fibers are preferably polymeric in structure so that they can provide mechanical strength, protection, and lubrication while encouraging tissue ingrowth. Such polymeric fibers include, for example, collagen, reticulin, elastin, cellulose, and biosynthetic analogs thereof. These fibers may be ordered in substantially circumferentially-extending or substantially radially-extending orientations, with the density of fibers being substantially uniform throughout the matrix. Alternatively, the matrix fibers may be unordered. In either the ordered or unordered configuration, the density of the fibers may be non-uniform. In the non-uniform configuration, relatively high densities of fibers may be established at anticipated points of high stress.

In an alternative aspect of the invention, the intrafibrillary (i.e., the space within the fiber) and interfibrillary (the space between the fibers) space is relatively high, a condition which promotes ingrowth of regenerated disc tissue. For example, the density of the intervertebral disc may be in the range of about 10–25 g matrix/cm$^3$. Alternatively, the intrafibrillary and interfibrillary space may be relatively low, a condition which provides superior cushioning, lubrication, and mechanical support for the intervertebral space, and which retards tissue and cell ingrowth, thereby diminishing the rate of scaffold resorption (e.g., density is in the range of about 2–10 g matrix/cm$^3$).

The temporary stability of the shape of the structure when in vivo, and the rate of disc resorption, are both attributed to the effective cross-link formation between at least one portion of the fibers. The cross-linking reagents used with the above-noted fiber materials may be any biocompatible, bifunctional reagents which interacts with amino, carboxyl, or hydroxyl groups on a single fiber forming intramolecular cross-links, or on multiple fibers or on the fibers and the GAGs, resulting in covalent bond formation between adjacent molecules (intermolecular cross-links). Useful cross-linking reagents include aldehydes, hexamethylene diisocyanate, bisimidates, polyglycerol polyglycidyl ether, acyl azide, and carbodiimides.

The cross-linked device maintains a sufficient degree of hydrophilicity and elasticity which simulates the properties of the natural intervertebral disc, i.e., ability to sustain mechanical stress and to protect and lubricate articular surfaces. In addition, the structure provides an ideal environment for cell infiltration and extracellular matrix synthesis and deposition, resulting in regeneration of natural disc tissue.

GAGs may be dispersed throughout the fibers. Alternatively, they may act as intermolecular cross-links between fibers. These GAGs typically include at least one of the group of molecules consisting of chondroitin 4-sulfate, chondroitin 6-sulfate, keratin sulfate, dermatan sulfate, heparan sulfate, heparin, and hyaluronic acid. The dispersion of GAG cross-links is preferably uniform, but may be more concentrated at anticipated points of high stress, typically at the peripheral region 14, and less concentrated in the central region 12 (FIG. 2). In such configurations, the GAG concentration may be in the range of about 0-25% in the distal region 14, and in the range of about 0-10% in the central region 12. However, when uniform, the dispersion of GAGs throughout the prosthetic intervertebral disc may be, for example, in the range of about 1-15%.

Intermolecular cross-links can also be established through a dehydrothermal process (heat and vacuum) which results in peptide bond formation between an epsilon amino group of lysine or hydroxylysine and a carboxyl group of aspartic or glutamic acid.

The cross-linked disc has a relatively high thermal stability at between about 55°-85° C., and preferably at between about 65°-75° C. for sufficient in vivo stability. This may be achieved through manipulation of the cross-linking conditions, including reagent concentration, temperature, pH, and time (see EXAMPLE 1).

In a one embodiment the prosthetic intervertebral disc is constructed mainly of Type I collagen fibers without GAG cross-links. Type I collagen fibers may be obtained from the Achilles tendons of animals. However, the fibers may also be obtained from animal skin or from the skin or tendon of humans. The tissues are treated with a series of mechanical and chemical means to either totally remove the non-collagenous materials or reduce them to a minimal level. In the preferred processing steps, the tendon or skin is mechanically disintegrated into fine pieces useful for further processing. The disintegration may be achieved by grinding the tissue at liquid nitrogen temperature, or by cutting the tissue into small pieces with a sharp knife. In certain applications, the tendons are mechanically disintegrated along the fiber direction in order to maintain the length of the fibers for mechanical strength.

Salt extraction of tendon at neutral pH removes a small portion of the collagen molecules that are newly synthesized and have not yet been incorporated into the stable fibrils. Salt also removes some glycoproteins and proteoglycans that are associated with collagen through electrostatic interactions. Other salts such as KCl can be used as a substitute for NaCl.

Lipids that are associated with the cell membranes or collagenous matrices may be removed by first extracting with detergents such as Triton X-100 (Sigma Chemical Co., St. Louis, Mo.), followed by extracting with ether-ethanol mixtures. The concentration of Triton X-100 is usually about 2-4%, but is preferably about 3%. The preferred mixture of ether-ethanol is usually at about a 1:1 ratio (v/v). The period of extraction is usually from 8 hours to 96 hours, and is preferably from about 24 to 48 hours.

Further extraction may be accomplished by matrix swelling conducted at two extreme PHs. Both acidic and basic swelling weakens the non-covalent intermolecular interactions, thus facilitating the release of non-covalently attached glycoproteins, GAGs, and other non-collagenous molecules through the open pores of the collagenous matrices.

The swelling of the collagenous matrix at alkaline pH is performed by treating the collagen at high pH with $Ca(OH)_2$, NaOH, or the like, for a period of about 8-96 hours. Alkali extraction in the presence of triple-helical stabilizing salts such as $(CH_3)NCl$ or $NH_3SO_4$ reduces the potential risk of denaturation of the collagen. Alkali treatment dissociates the non-cross-linked glycoproteins and GAGs from the collagen matrices. The alkali also removes the residual lipids through saponification.

Acid swelling may be conducted at a low pH in the presence of acetic acid, HCl, or similar acids. Like the alkali treatment, the swelling removes non-cross-linked glycoproteins and GAGs.

The non-triple helical portions of the molecule (telopeptides) are involved in intermolecular cross-linking formation. They are weak antigens and are susceptible to attack by proteases such as pepsin and trypsin. Prolonged digestion with such proteases dissociates the fibrils (fibers) into individual molecules. However, if the digestion process is properly controlled such that maximal telopeptides are removed without complete dissociation, the immunogenic properties of the fibrils can be reduced to a minimal level without compromising the mechanical strength. For example, to isolate molecular collagen, the digestion of skin or tendon with pepsin is usually conducted at an enzyme:collagen ratio of about 1:10 for about 24-96 hours at below room temperature. In comparison, fibrils may be obtained by limited pepsin digestion achieved at a ratio of about 1:100 (enzyme:collagen) for about 24-96 hours at 4° C.

Collagen fibers obtained according to this methodology are then used to fabricate the prosthetic intervertebral disc of the present invention. However, it must be appreciated that collagen obtained from other sources, such as biosynthetically-produced collagen or analogs thereof, may also be used in the construction of the prosthetic intervertebral disc.

One method of fabrication includes molding the collagen fibers into a predetermined shape using, for example, the mold forms described below in conjunction with FIGS. 6 and 7. The fibers may be placed randomly in the mold, or may be oriented in specific directions to achieve a intervertebral disc having specific structure characteristics. Other components such as GAGs which may participate in the cross-linking reaction, can be mixed in with the fibers in a random or non-random fashion before the structure is subjected to various cross-linking procedures including chemical methods and/or dehydrothermal methods.

By following the processes described in the examples set forth hereinbelow, a prosthetic intervertebral disc of the form shown in FIGS. 2 or 3 may be constructed having the characteristics listed below in TABLE 1.

TABLE 1

| Physical Characteristics |
|---|
| height A = 5-12 mm |
| radius C = 10-25 mm |
| density = 0.07-0.5 $g/cm^3$ |
| intra- and interfibrillary space = 2-25 $cm^3/g$ matrix |
| Constituents |
| fiber content = 75-100% |
| glycosaminoglycan content = 0-25% |

The prosthetic discs were evaluated in vivo and in vitro to determine ability to function physically, or to serve as a regeneration template for the fibrochondrocytes expected to serve as precursor cells for the subsequent fibrocartilaginous matrix. These studies demonstrate that the prosthetic disc allows for, and induces fibrochondrocyte infiltration and disc regeneration through the prosthetic material.

The following non-limiting examples describe methods of fabrication and in vivo use of the prosthetic intervertebral disc of the present invention.

EXAMPLE 1

Mold Fabrication

A mold useful for fabricating the prosthetic intervertebral disc is made of implantable stainless steel or biocompatible plastics such as polypropylene, delrin, or combination of these materials. Exemplary mold 100 is composed of three pieces 102, 104, and 106 as shown in FIGS. 6 and 7.

Figure 7:
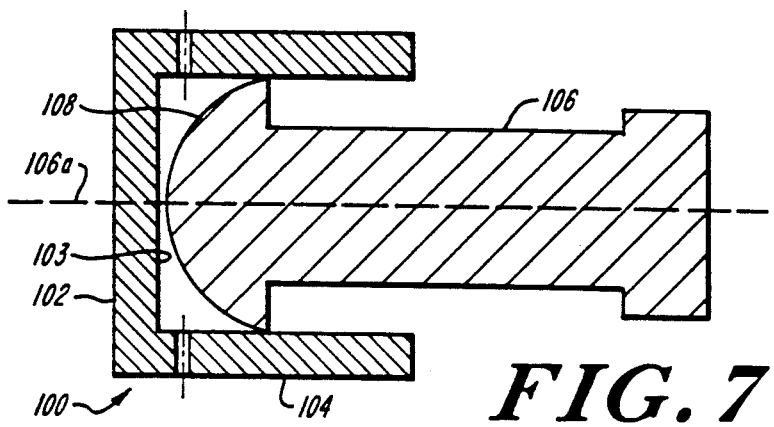
FIG. 7 shows in section an alternative mold for constructing a prosthetic intervertebral disc.

By way of example for the disc-shaped intervertebral disc illustrated in FIGS. 5A and 5B, the mold 100 of FIG. 7 is used. Piece 102 is disc-like and has a diameter substantially equal to that of the desired intervertebral disc. Piece 102 is perforated to allow liquid to pass through under pressure. The inner surface 103 of piece 102 has the desired shape of one side of the intervertebral disc-to-be-formed.

Piece 104 is a hollow cylinder which has the same inner dimension as piece 102. Piece 106 is a cylindrical piston which has an outer diameter slightly less than the inner diameter of piece 104. The "top", or crown, surface 108 of piston 106 has the desired shape of one side of the intervertebral disc-to-be-formed.

Figure 6:
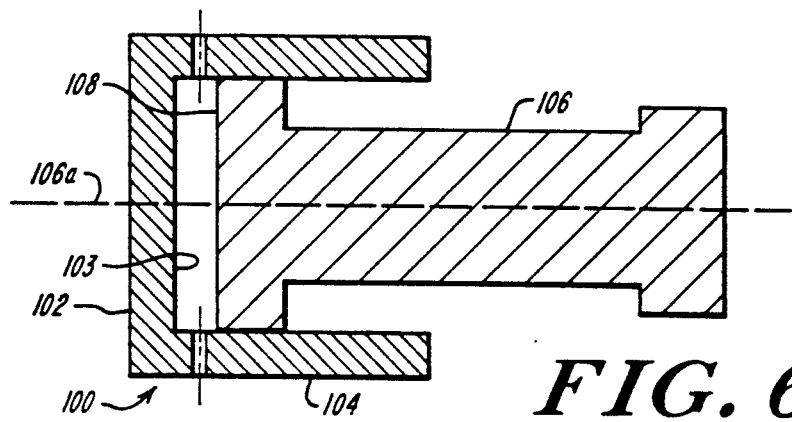
FIG. 6 shows in section an exemplary mold for constructing a prosthetic intervertebral disc.

For an intervertebral disc having flat top and bottom surfaces, the mold 100 of FIG. 6 is used where pieces 102 and 104 are the same as pieces 102 and 104 in FIG. 7, and piece 106 is similar to piece 106 in FIG. 7 but has a flat crown surface 108.

During fabrication of the prosthetic disc 220, mold piece 102 is first assembled within piece 104, as shown in FIG. 6. The constituent fibers (in a fluid) are placed against the surface 103 of piece 102. The crown surface 108 of piston 106 is then driven toward surface 103 along a compression axis until the fibers are compressed, the fluid is driven out through piece 102, and the desired axial dimension of the compressed fiber array is attained. The mold is then frozen in preparation for cross-linking.

EXAMPLE 2

Preparation of Purified Type I Collagen

Bovine, porcine, or sheep Achilles tendon is obtained from USDA-approved slaughter houses. The preferred age of the animals is between 12–18 months. The tissue is kept cold during the purification process except where specified to minimize bacteria contamination and tissue degradation.

The adhering tissues of carefully selected tendons are first scrapped off mechanically. The tendons are then minced or cut into fine pieces and washed in excess quantities (about 10 volumes) of cold water to remove residual blood proteins and water soluble materials.

The washed tendons are extracted in ten volumes of 5% NaCl, 0.01M Tris, pH 7.4, for 24 ($\pm$4) hours to remove salt soluble materials. The salt-extracted tendons are repeatedly washed in about 10 volumes of water to remove the salt.

To extract lipid, the material is extracted in 3% Triton X-100 for 24 ($\pm$2) hours. The detergent is removed by extensive washing with water. The material is then extracted in 3–4 volumes of ether-ethanol (1:1 vol/vol) for 24 ($\pm$2) hours to further minimize the lipid content. The lipid extracted material is extensively washed in water to remove the ether and ethanol.

The material is then subjected to two extreme pH extractions to remove non-collagenous materials. Alkaline extraction is conducted with 3–4 volumes of 0.2M NaOH at pH 12.5–13.5 at room temperature in the presence of 1.0M $(CH_3)NCl$ for 24 ($\pm$2) hours with mild agitation.

Following alkaline extraction, the pH is neutralized with HCl, and the material is washed with water. The pH is then adjusted to 2.5–3.0 by adding concentrated acetic acid to a final concentration of 0.5M. The acid extraction is continued for 24 ($\pm$2) hours with agitation.

The acid swollen tendon is then subjected to a limited proteolytic digestion with pepsin (enzyme:collagen = 1:100) for 24 ($\pm$) 2 hours. The pepsin and resulting telopeptides are removed through dialysis.

The swollen fibrillar material is then coacervated by adjusting the pH to its isoionic point with 1M NaOH or HCl or by adjusting the ionic strength to 0.7 with NaCl. The aggregated collagen fibers are harvested by filtration, and the filtered material extensively washed with cold phosphate buffered saline solution. The highly purified type I collagen may be stored at $-20°$ to $-40°$ C. until used.

EXAMPLE 3

Device I Fabrication

A) The collagen content of the highly purified type I collagen fibrils from EXAMPLE 2 is determined either by gravimetric methods or by determining the hydroxyproline content assuming a 13.5% by weight of hydroxyproline in Type I collagen. The amount of purified material needed to fabricate a given density of a prosthetic intervertebral disc device is then determined and weighed out.

B) A solution of fibrillar collagen is carefully fit into a mold of desired, specified dimensions (see EXAMPLE 1 and FIG. 6 for a description of molds). Collagen fibers are laid down in random manner or in an oriented manner. In the oriented manner, circumferential orientation of the fibers is produced by rotation of the piston about its principal axis as the material is compressed in the mold; radial orientation is produced by manual painting of the collagen fibers in a linear, radially directed fashion.

C) The fibers are frozen at $-20°$ C., turned out of the mold, and thawed at room temperature.

D) The fibers are then resuspended in phosphate buffered saline, put back into the mold in the desired orientation(s), and compressed with the piston.

E) The compressed fibers are then refrozen at $-20°$ C. and then thawed at room temperature.

F) The resulting structure is cross-linked by soaking in a 0.2% glutaraldehyde solution, pH 7.6, for 24 ($\pm$0.5) hours. Each glutaraldehyde-cross-linked prosthetic disc is subsequently rinsed repeatedly in 500 ml of phosphate buffered saline (PBS) solution PH 7.4, for 4, 8, 24 and 48 hours.

G) The rinsed matrix is then lyophilized.

EXAMPLE 4

Device Fabrication

A)-E) same as EXAMPLE 3)

F) The structure is immersed in an aqueous solution of 0.5M sodium nitrite, 0.3M Hcl, and Nacl (OM, 0.34M, 1.0M, or 1.34M) for 3 minutes at 4° C.

EXAMPLE 5

Device II Fabrication

A)-G) (same as in EXAMPLE 3)

H) The lyophilized matrix is subjected to dehydrothermal cross-linking by vacuum and heat. The vacuum is first applied to reduce the residual water content to a minimal level. Some structural water (about 3%) may still be associated with collagen triple-helix as part of the structure stabilizing factor. The heat is increasing in steps to 110° C. (±5°), and continually applied at 110° C. under vacuum for 24 (±2) hours.

EXAMPLE 6

Device III Fabrication

A) (same as in EXAMPLE 3)

B) The collagen material is dispersed in 0.01M HCl at pH 2.0–2.5. Predetermined amounts of various GAGs are weighed and dissolved in water. For example, for a given density of 0.25 g/cm$^2$, the collagen content will be 0.244 g, the hyaluronic acid content will be 0.003 g, and the chondroitin sulfate content will be 0.003 g for a 2.5% GAG content. The GAG solution is mixed in with the collagen solution and placed in the mold in the desired orientation as described in EXAMPLE 2.

C)–G) (same as in EXAMPLE 3)

EXAMPLE 7

Device IV Fabrication

A)–C) (same as in EXAMPLE 3)

D) (same as in EXAMPLE 3 except that the fibers laid down are not compressed.

E)–G) (same as in EXAMPLE 3)

EXAMPLE 8

Device V Fabrication

A)–E) (same as in EXAMPLE 3)

F) The molded collagen is cross-linked in 5% polyglycerol polyglycidyl ether in 50% ethanol and 0.1M Na$_2$CO$_3$ at PH 10.0 for 24 (±2) hours. The cross-linked device is rinsed for 4, 8, 24 and 48 hours, each with 500 ml of PBS, pH 7.4.

G) (same as in EXAMPLE 3)

EXAMPLE 9

Device VI Fabrication

A)–E) (same as in EXAMPLE 3)

F) The molded collagen is cross-linked in the presence of 1-ethyl-3-(3-dimethylaminopropyl) carbodiimide (10 mg/g matrix) in 0.9% NaCl, pH 4.7 at room temperature for 24 (±2) hours. The addition of carbodiimide is made every 3–4 hours, and the pH is adjusted to 4.7 after each addition of carbodiimide.

G) (same as in EXAMPLE 3)

EXAMPLE 10

Device VII Fabrication

A)–D) (same as in EXAMPLE 2)

E) For attachment purposes, a mesh of absorbable polyglyconate suture material, matched to the size of the mold, is laid in the dispersed collagen such that it protrudes from the structure's periphery to form a skirt which may extend over the vertebral body. This mesh provides both immediate attachment sites and long term fibrous ingrowth.

F)–G) (same as in EXAMPLE 2)

EXAMPLE 11

In vitro Testing

Intervertebral discs are aseptically harvested from mature goats or dogs, trimmed of all adherent tissue, and placed into Gey's balanced saline solution. Each disc is bisected in the coronal plane and 3 mm full-thickness circular defects are made in each half. The defects are filled with a 3 mm diameter plug of one of two prototypes of a complex collagen-based matrix. The discs are placed in six well culture plates containing 6 ml of Dulbecco's Modified Eagle's Medium supplemented with 10% fetal bovine serum, sodium ascorbate, and 0.1% penicillin/streptomycin. Cultures are maintained at 37° C. in a humidified atmosphere of 10% CO$_2$/90% air, fed three times per week, and placed in fresh culture wells every week to prevent the formation of explant cell cultures. At intervals of one, four, and six weeks after initiation of culture, three discs from each group are removed, fixed, and evaluated with serial sections and staining. New collagen and glycosaminoglycan formation is evidenced histologically using Alcian Blue and Masson's Trichrome stains.

The results demonstrate increasing cellular migration and invasion over time. There is no apparent toxicity from the material. The depth of cellular penetration into the scaffold appears to be limited by the density of the prosthetic complex.

EXAMPLE 12

In vivo Testing

The cervical vertebral disc of a mature goat was primarily excised and surgically replaced by a prosthestic disc. The goat returned to full cage activities within a day after surgery. Serial radiographs have documented preservation of the intervertebral joint space.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for fabricating a prosthetic intervertebral disc comprising the steps of:
   (a) placing a plurality of biocompatible and bioresorbable fibers into a mold such that said fibers assume the shape of said mold, said mold having a shape that enables disc function;
   (b) subjecting said fibers to a first and a second cycle of freezing and thawing;
   (c) contacting said fibers with a chemical cross-linking agent to cross-link said fibers; and
   (d) lyophilizing said cross-linked fibers,
   whereby said fibers form a dry porous volume matrix being adapted to have in vivo an outer surface contour substantially the same as that of the natural intervertebral disc,
   whereby said matrix establishes an at least partially bioresorbable scaffold adapted for ingrowth of vertebral fibrochondrocytes such that said scaffold and said ingrown vertebral fibrochondrocytes are capable of supporting natural intervertebral load forces.

2. The method of claim 1 wherein said placing step comprises placing a plurality of fibers into a mold, said fibers including a natural material, an analog thereof, or a synthetic material.

3. The method of claim 2 wherein said analog of said natural material is a biosynthetic analog.

4. The method of claim 1 wherein said placing step further comprises placing a plurality of polymeric fibers into said mold.

5. The method of claim 1 wherein said fibers are selected from the group consisting of collagen, elastic, reticulin, cellulose, analogs thereof, and mixtures thereof.

6. The method of claim 1 wherein said placing step further comprises placing a plurality of glycosaminoglycan molecules into said mold.

7. The method of claim 6 wherein said glycosaminoglycan molecules are selected from the group consisting of chondroitin 4-sulfate, chondroitin 6-sulfate, keratin sulfate, dermatan sulfate, heparin, heparan sulfate, hyaluronic acid, and mixtures thereof.

8. The method of claim 1 wherein said placing step further comprises the step of orienting said fibers substantially circumferentially.

9. The method of claim 8 wherein said orienting step comprises compressing said fibers in said mold with a piston, directed along a compression axis, while during said compressing step said piston is rotated with respect to said mold about said compression axis.

10. The method of claim 8 wherein said orienting step comprises rotating said mold as said fibers are placed therein.

11. The method of claim 1 wherein said placing step further comprises the step of orienting said fibers substantially radially.

12. The method of claim 1 further comprising the step of compressing said fibers prior to said second cycle of freezing and thawing.

13. The method of claim 6 further comprising the step of compressing said fibers and said GAGs prior to said second cycle of freezing and thawing.

14. The method of claim 12 wherein said compressing step comprises applying a predetermined amount of pressure to a region of said matrix with a piston, said piston having a predetermined shape.

15. The method of claim 1 wherein said chemical cross-linking agent is selected from the group consisting of glutaraldehyde, formaldehyde, biocompatible and bifunctional aldehydes, carbodiimides, hexamethylene diisocyanate, bisimidates, polyglycerol polyglycidylether, glyoxal, acyl azide, and mixtures thereof.

16. The method of claim 1 further comprising the additional step of subjecting said lyophilized matrix to dehydrothermal cross-linking.

* * * * *